United States Patent [19]

Gerstein

[11] Patent Number: 4,986,983

[45] Date of Patent: Jan. 22, 1991

[54] SUPERFATTED BETAINE AND ZWITTERIONIC HAIR AND SKIN CONDITIONER COMPOSITIONS

[75] Inventor: Terry Gerstein, East Brunswick, N.J.

[73] Assignee: Revlon, Inc., New York, N.Y.

[21] Appl. No.: 332,698

[22] Filed: Apr. 3, 1989

[51] Int. Cl.⁵ .................................. A61K 1/06
[52] U.S. Cl. .......................... 424/070; 252/546; 252/657; 514/844
[58] Field of Search ............ 514/772, 788, 844; 424/70, 63; 252/546, 547

[56] References Cited

U.S. PATENT DOCUMENTS

| | | | |
|---|---|---|---|
| 3,328,307 | 6/1967 | Schmitz | 252/106 |
| 3,449,430 | 6/1969 | Dohr et al. | 260/583 |
| 3,822,312 | 7/1974 | Sato et al. | 252/527 |
| 3,876,760 | 4/1975 | Nersesian et al. | 424/70 |
| 3,928,251 | 12/1975 | Bolich et al. | 252/545 |
| 3,959,463 | 5/1976 | Nersesian et al. | 424/70 |
| 3,960,742 | 6/1976 | Leonard | 252/90 |
| 3,980,769 | 9/1976 | Ghilardi et al. | 424/70 |
| 4,020,155 | 4/1977 | Kalopissis et al. | 424/70 |
| 4,080,310 | 3/1978 | Ng et al. | 252/544 |
| 4,107,328 | 8/1978 | Michaels | 424/316 |
| 4,110,263 | 8/1978 | Lindemann et al. | 252/545 |
| 4,138,427 | 2/1979 | Vanlerberghe et al. | 260/459 |
| 4,148,762 | 4/1979 | Koch et al. | 252/544 |
| 4,166,845 | 9/1979 | Hansen et al. | 424/78 |
| 4,221,733 | 9/1980 | Melloh et al. | 260/404.5 |
| 4,294,728 | 10/1981 | Vanlerberghe et al. | 252/542 |
| 4,342,742 | 8/1982 | Sebag et al. | 424/59 |
| 4,348,292 | 9/1982 | Ginn | 252/90 |
| 4,370,272 | 1/1983 | Wechsler et al. | 260/404 |
| 4,375,421 | 3/1983 | Rubin et al. | 252/110 |
| 4,420,410 | 12/1983 | Huttinger | 252/117 |
| 4,420,484 | 12/1983 | Gorman et al. | 424/326 |
| 4,452,989 | 6/1984 | Deckner et al. | 548/537 |
| 4,507,280 | 3/1985 | Pohl et al. | 424/70 |
| 4,526,781 | 7/1985 | Goldberg et al. | 424/70 |
| 4,534,877 | 8/1985 | Russell et al. | 252/106 |
| 4,590,069 | 5/1986 | Deckner et al. | 424/70 |
| 4,631,187 | 12/1986 | Padden et al. | 424/70 |
| 4,636,329 | 1/1987 | Steuri | 252/106 |
| 4,663,158 | 5/1987 | Wolfram et al. | 424/70 |
| 4,714,610 | 12/1987 | Gerstein | 424/70 |

FOREIGN PATENT DOCUMENTS

| | | |
|---|---|---|
| 0854994 | 11/1960 | United Kingdom . |
| 1547361 | 6/1979 | United Kingdom . |
| 2057883 | 4/1981 | United Kingdom . |

OTHER PUBLICATIONS

Chemical Abstract 88: 172314p (1978) Tsutsumi et al., "Shampoo Composition with Low Skin Irritation".

*Primary Examiner*—Merrell C. Cashion, Jr.
*Assistant Examiner*—Amy Hulina

[57] ABSTRACT

This invention relates to compositions which are useful for improving the texture, feel and appearance of hair and skin. More particularly, this invention relates to conditioning compositions which are typically applied to the hair and skin subsequent to a cleansing treatment.

7 Claims, No Drawings

SUPERFATTED BETAINE AND ZWITTERIONIC HAIR AND SKIN CONDITIONER COMPOSITIONS

FIELD OF THE INVENTION

This invention relates to compositions which are useful for improving the texture, feel and appearance of hair and skin. More particularly, this invention relates to conditioning compositions which are typically applied to the hair and skin subsequent to a cleansing treatment.

Hair conditioning agents assist in the control and management of hair. Conditioned hair is easily untangled and combed through after shampooing, lays orderly when dry and provides a favorable feeling to the touch. The conditioning action on hair, particularly by cationic conditioning agents, is believed to be caused by the attraction of the positively charged agent to the negatively charged sites on hair protein resulting in the deposition of the agent onto the hair fiber. After washing hair and during the subsequent management of the dry hair, the combing and brushing forces produce friction resulting in the accumulation on the hair's surface of immobile electrons or ions of the same charge. The hair is commonly referred to as containing static charge and displays the phenomenon of "fly-away". Such hair is unruly, will not lay flat and is considered generally unmanageable.

Ionic depositions including positively charged cationic conditioning agents can be used to dissipate static electricity by increasing the mobility of the electrostatic charges that accumulate on hair. Furthermore, the fatty nature of the cationic conditioning agent produces lubrication on the hair's surface that reduces friction (triboelectric friction) resulting in the overall lessening of accumulated electrostatic charges and the promotion of easy combing. The process by which cationic surfactants are applied to hair is referred to as conditioning the hair, and the treatment results in hair that no longer sustains a static charge and in hair that also feels soft, silky and is highly manageable.

Cationic surfactants have been used extensively as hair conditioning agents in creme rinses and occasionally in shampoos, generally at pH levels below pH 7 in creme rinses and through pH 7 and above in shampoos when the formula permits. In the past, best results in creme rinses have been obtained with cationic surfactants that are long chain high molecular weight quaternary ammonium compounds or long chain fatty amine salts. For example, stearalkonium chloride has been widely used as a component of creme rinse hair conditioning formulations. The positive charge of the quaternary surfactant is attracted to the negatively charged surface of the hair protein; the surfactant deposits on the surface and subsequently renders the hair manageable. The long chain constituent on the quaternary surfactant coats the hair fiber giving it lubricity during wet combing and a desirable texture after drying. The longer the chain length the more active the conditioning agent is said to be; the greater the residual film deposit on hair the easier the detangling effort and the less electrostatic charge build-up and subsequent hair fly-away.

Quaternary ammonium compounds carry and maintain positive ionic charges in media having highly alkaline to highly acidic pH. However, many industrial quaternary ammonium compounds are partially or totally unsuitable for cosmetic use because they can contain impurities which restrict use to specific pH ranges or restrict use completely. If trace quantities of deleterious quaternizing agents used in synthesis are present, the quaternary ammonium compound should not be used in cosmetics. Long chain fatty amines, which usually account as significant impurities in the quaternary ammonium compounds used for cosmetics, force the use of the quaternary ammonium compound, and the cosmetic itself, to pH's below 7. Below pH 7, the long chain amines exist as surface active salts which produce hair conditioning effects which are similar to those produced by surface active quaternary ammonium salts. Above pH 7, the amine salts revert to their free organic amine state which cause them to loose their hair conditioning properties, to produce cosmetically unaesthetic odors and appearances, and to increase irritation to the skin and eyes.

Amine oxides, which act as nonionic materials in alkaline media and weakly cationic materials in acidic media, have been reported in U.S. Pat. No. 4,714,610 to exhibit effective hair conditioning properties in compositions having a pH of about 2.4 to about 3.8 which is described as the isoelectric point of hair. As described in the aforesaid patent, the mechanism for the conditioning effect obtained from the amine oxide material is not clear in view of the neutral state of the hair protein at its isoelectric point.

This invention is related to the use of amphoteric materials, such as betaines and zwitterionic analogues thereof, in compositions useful for conditioning hair and skin.

REPORTED DEVELOPMENTS

Generic disclosures of low pH betaine and/or zwitterionic-containing compositions are included in U.S. Pat. Nos. 4,080,310; 4,107,328; 4,294,728; 4,507,280; 4,526,781; 4,534,877; and 4,663,158.

U.S. Pat. No. 4,294,728 to Vanlerberghe, assigned to L'Oreal, discloses that foaming compositions can have a pH of 2.5–10.5, and that shampoo compositions have a preferred pH of 3 to 9.5. The Vanlerberghe foaming and cleaning compositions, which are reported to exhibit good conditioning properties, comprise a variety of surfactants including amphoteric surfactants and a 1,2 alkane diol, which is disclosed to be an essential synergistic ingredient. Not a single example of a betaine-containing composition of pH less lo than 4 is disclosed.

The prior art discloses specific zwitterionic- or betaine-containing compositions having a pH less than 4 in U.S. Pat. Nos. 4,636,329 and 4,375,421, but these compositions do not include a superfatting material.

Zwitterionic- or betaine-glycinate containing compositions which include a superfatting agent are disclosed in U.S. Pat. Nos. 3,822,312; 3,928,251; 4,020,155; 4,420,410; 4,420,484; and 4,526,781 and in British Pat. No. 854,994, but none of these patents discloses even generically that the pH of the composition could be as low as 4.

The present applicant has discovered that excellent conditioning properties may be obtained with a zwitterionic- or betaine-containing composition having characteristics apparently overlooked by the prior art.

SUMMARY OF THE INVENTION

This invention relates to a composition, for conditioning the hair or skin, having a pH of about 2 to about 3.5 and including a betaine or zwitterionic compound and a superfatting material. Applicant has discovered that the incorporation of a superfatting material in a zwitterionic- or betaine-containing composition of low pH transforms it into a surprisingly effective conditioning composition.

This invention also relates to a method for conditioning the hair or skin comprising the application to the hair or skin of the aforesaid composition.

DETAILED DESCRIPTION

The following terms as used herein are defined below.

"Betaine" means an N-alkylcarboxylate-N-fatty alkyl-quaternary amine.

"Zwitterionic compound" means an N-alkylcarboxylate-N'-fatty alkyl-ammonium compound.

"Superfatting material" means a fatty alcohol, fatty acid or alkyl ester of a fatty alcohol, which are the organic carboxylic acids or derivatives thereof of a long chain alkyl or are derived from a naturally occurring oil or fat or a hydrogenated product thereof including coconut oil, castor oil, palm kernel oil, cottonseed oil, peanut oil, olive oil, palm oil, sunflower seed oil, sesame oil, corn oil, safflower oil, poppyseed oil, teaseed oil, kapok oil, rice bran oil, grain sorghum oil, rapeseed oil, linseed oil, soybean oil, perilla oil, hempseed oil, wheatgerm oil, rubberseed oil, tung oil, oiticica oil, cacahuanache oil, whale oil, pilchard oil, Japanese sardine oil, menhaden oil, herring oil, fish liver oil, tallow, milk fat or lard.

"Alkyl" means an aliphatic hydrocarbon, either straight or branched chain, and having from one to about 20 carbon atoms. Preferred alkyl groups have from one to about 8 carbons atoms. The most preferred are the "lower alkyl" groups which have from one to about six carbon atoms.

"Long Chain Alkyl" means an aliphatic hydrocarbon, either straight or branched chain, and having from about 13 to about 20 carbon atoms.

"Fatty Alkyl" means a long chain alkyl radical. Preferred fatty alkyl groups are derived from fatty alcohols obtained by purifying a fatty material derived from natural sources.

"Amido Radical" means a group of the formula $$-CO-N\begin{matrix}R\\|\end{matrix},$$

where the R substituent group may be hydrogen, alkyl or fatty alkyl.

Examples of betaine and zwitterionic compounds are described by the formula:

$$R_1-Z-(C)_x-N^+-(CH_2)_y-C-O^-$$
with $R_2$, $R_3$ on C and $R_4$, $R_5$ on N   FORMULA I wherein:
$R_1$ is fatty alkyl;
x is from 1 to about 3;
y is from 1 to about 6;
$R_2$, $R_3$, $R_4$ and $R_5$ are hydrogen, alkyl or hydroxyalkyl;
$R_4$, $R_5$, $R_6$ and $R_7$ may also form a nitrogen-containing ring together with the carbon and nitrogen atoms to which they are attached; and
Z represents an amido radical group or a carbon-carbon single bond.

A preferred betaine compound according to Formula I is wherein Z is a single bond, $R_2$ and $R_3$ are hydrogen and $R_4$ and $R_5$ are not hydrogen.

Preferred zwitterionic compounds are according to Formula I wherein $R_4$ is hydrogen.

The betaine and zwitterionic compounds may be prepared by methods well known in the art, for example, by reaction of the corresponding secondary or tertiary amine with an alkylating agent, such as chloroacetic acid, or by reaction of an alkyl halide with a starting amine that includes the alkylcarboxylate group.

A special class of betaines for use in this invention include lauryl dimethyl amine glycinate, myristyl dimethyl amine glycinate, cetyl dimethyl amine glycinate, stearyl dimethyl amine glycinate, oleyl dimethyl amine glycinate, heptadecyl dimethyl amine glycinate, behenyl dimethyl amine glycinate, dimethyl cocamine glycinate, dimethyl hydrogenated tallow amine glycinate, bis (hydroxyethyl) cocamine glycinate, bis (hydroxyethyl) tallow amine glycinate, bis (hydroxypropyl) stearamine glycinate, bis (hydroxymethyl) behenamine glycinate, pentadecyl diethyl amine glycinate, tridecyl dipropyl amine glycinate, tridecyl bis (2-hydroxybutyl) amine glycinate, heptadecyl bis (2-hydroxybutyl) amine glycinate and tridecyloxypropyl bis (hydroxyethyl) amine glycinate.

Another special class of betaines include the propionate analogs of the aforementioned glycinate betaines.

Examples of betaine compounds which are specially preferred comprise one or more of hydrogenated tallow dimethyl glycinate, dihydroxyethyl tallow glycinate or stearamido ethyl ethanolamine glycinate.

Another class of betaines include, dicoco methyl amine glycinate, distearyl methyl amine glycinate, dihydrogenated tallow methyl amine glycinate, dicetyl methyl amine glycinate, cetyl isocetyl methyl amine glycinate, lauryl cetyl methyl amine glycinate, dilinoleyl methyl amine glycinate, disoya methyl amine glycinate, diisostearyl methyl amine glycinate, distearyl hydroxyethyl amine glycinate, stearyl, isostearyl hydroxymethyl amine glycinate, hexyl bis (2-hydroxyhexadecyl) amine glycinate and distearyl hydroxypropyl amine glycinate.

Another class of amido-containing betaines include cocylamido-propyl dimethyl amine glycinate, myristoylamidopropyl dimethyl amine glycinate, stearoylamidoethyl dimethyl amine glycinate, linoleoylamidopropyl dimethyl amine glycinate, hydrogenated tallow amidoethyl bis (hydroxyethyl) amine glycinate, palmitoylamidoethyl bis (hydroxypropyl) amine glycinate, stearoylamidopropyl dimethyl amine glycinate, and hydrogenated tallow amidopropyl dimethyl amine glycinate.

Still another class of betaine or zwitterionic compounds includes the imidazoline betaines and zwitterionics of the formula:

(imidazoline ring with $R_1$ substituent on ring carbon, $N^+$ with $R_2$ and $R_3$ substituents)

wherein $R_1$ and $R_2$ are hydrogen, a long chain alkyl group, 2-hydroxyethyl, a derivative of 2-hydroxyethyl or a nonionic derivative of 2-aminoethyl, and $R_3$ is an alkylcarboxylate group.

Examples of suitable imidazoline betaines of this class include 1-hydroxyethyl-2-heptadecenyl-2-imidazoline-1-glycinate, 1-hydroxyethyl-2-heptadecanyl-2-imidazoline-1-glycinate, 1-acetylhydroxyethyl-2-tridecanyl-2- imidazoline-1-glycinate, 1-acetylaminoethyl-2-tridecanyl-2-imidazoline-1-glycinate, and 1-ethoxyethyl-2-pentadecanyl-2-imidazoline-1-glycinate Yet another suitable class of compounds includes the morpholino compounds of the formula:

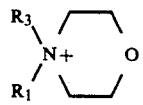

wherein $R_1$ is hydrogen or a long chain alkyl group and $R_3$ is an alkylcarboxylate.

Examples of suitable betaines of this class include N-2-hydroxymenyl-morpholine glycinate, N-2-hydroxy-pentadecyl-morpholine glycinate, and N-2-hydroxyheptadecyl-morpholine glycinate.

Good results are obtained when the betaine or zwitterionic compounds are used at a concentration of between about 0.5% and about 15% by weight of the conditioner formulation. The preferred concentration is about 1.5% to about 8% of the compound by weight of the hair conditioning composition.

The conditioning composition includes also a superfatting material which is selected preferably from the group consisting of fatty acids, fatty alcohols or fatty acid alkyl esters. A most preferred superfatting material is cetyl alcohol.

A preferred embodiment of this invention comprises a composition which includes said betaine or amphoteric compound and said superfatting material in effective hair- and skin-conditioning amounts.

More specifically, preferred amounts of superfatting materials are about 0.5 to about 5 weight percent of said composition.

A preferred pH of the composition according to this invention is within a range of about 2.2 to about 3.2, with a most preferred pH range of about 2.5 to about 3.

In general, the composition is prepared by admixing the betaine or zwitterionic compounds, superfatting material, water and sufficient acid, for example, hydrochloric acid, to reduce the pH within the aforesaid range. Other acids that may be used include phosphoric acid and those organic acids (acetic, citric, glycolic, etc.) that offer sufficient acidity to accommodate the low pH range.

Other ingredients may be added to the conditioning composition for the purpose of performing desired functions. For example, ethoxylated cetyl alcohol which is an emulsifier, and other materials such as hydrolyzed proteins, perfumes, colorants and preservatives may be added as desired.

The following examples are illustrative of the present invention. Various of the ingredients essential to the composition may be varied in amount within the limits described herein.

EXAMPLE 1

Hydrogenated tallow dimethyl glycinate, a betaine, is used at 6.4% active concentration in an aqueous dispersion also including 1% cetyl alcohol. The "gloppy" highly pearlized creme which resulted did not display any pronounced conditioning effect when applied to hair and rinsed off.

Phosphoric acid is added to the aforementioned composition in an amount sufficient to lower the pH to 2.7. A more fluid composition is obtained. The low pH composition exhibits heightened conditioning effects after application and rinsing thereof on hair and skin of the hands.

EXAMPLE 2

The following is a formulation of a composition according to this invention.

| Dihydroxyethyl tallow glycinate (40% active) | 21.0 |
| --- | --- |
| Phosphoric acid | 1.0 |
| Cetyl alcohol | 2.0 |
| Color, fragrance, preservative | qS |
| Water | qS 100 |

The glycinate, acid and alcohol are weighed into a beaker and melted. Water at 80° C. is added. The aqueous mixture is mixed and slowly cooled to 43° C. Fragrance, color and preservative are added at ambient temperatures.

During cooling, pearlescence develops and the product turns from fluid at warmer temperatures to a pituitous semi-gel at room temperature. Final pH is 2.9.

The preparation is tested as a rinse-off hair conditioner and is evaluated against a commercial hair conditioner. It produces the same order of conditioning response as the popularly sold conditioner, but differs in that the hair is left feeling cleaner with more body. When the product is massaged into the hands and rinsed away, the dried hands display unusual, highly perceptible smoothness, a smoothness not recognized with the incidental use of other hair conditioners.

EXAMPLE 3

A formula corresponding to that described in Example 2 is prepared using stearamido ethyl ethanolamine glycinate at 6% active concentration. This product shows also hair and skin conditioning effects.

The present method comprises the application of the applicant's composition to hair or skin, previously moistened with water, and distributing the composition throughout the hair or skin to permit even distribution. Application should involve rubbing or combing. The composition should be permitted to remain on the hair for a period of time sufficient to allow even distribution, for example, from 5 to 30 seconds. The composition should be rinsed from the hair or skin with water.

The conditioning properties of the present composition may be evaluated by using the following test procedures.

1. Procedure for Evaluation

A 2 gram, 10" long tress of double bleached hair is shampooed with a conventional shampoo, and reshampooed again to simulate a double shampoo typical of consumer use. The hair is rinsed thoroughly under the tap with tepid water. Five cc of a test hair conditioner is measured with a syringe and applied to the hair tress. The conditioner is worked into the hair tress for a minute and then the tress is rinsed with tepid water under the tap for one minute. The hair is touched, observed, combed, smelled and rated to a control shampooed tress without a conditioner application. Upon drying, the tress is treated again by touching, observing, combing and smelling.

Tests to determine the substantivity of the betaine or zwitterionic compound to hair protein are conducted using the "Rubine Dye Test". The dye test for determining substantivity of cationics to hair demonstrates the degree of the adhesive nature of a cationic agent to hair during rinsing with water. Hair treated with a cationic conditioner will gather a rinse-fast stain when subjected to the dye; the coloration gathered on untreated hair is readily rinsed away. The dye complexes with positively charged surfactant residues on the hair forming a stain that resists rinsing from the hair. Pyrazole Fast Bordeau 2 BL was used in these tests in place of Rubine dye. The betaines and zwitterionic compounds used in this invention produce a positive Rubine Dye Test response on tresses treated with formulations described herein.

The Rubine Dye Test employed a double bleached hair tress which is treated with the present composition. After treatment, the tress is rinsed for exactly one minute under tepid tap water. The tress is then towel-dried and immersed in a 0.2% aqueous Pyrazol Fast Bordeau 2 BL dye solution for 10 seconds. Again, the tress is rinsed under the tap to remove excess dye solution from the hair. A residual red stain left on the hair indicates a substantive deposition of betaine or zwitterionic compound. No red stain appears on a free-rinsed control hair tress that is not treated prior to treatment with dye.

The hair conditioning delivered by the compositions of this invention have properties that are variable accordingly, adjustments in formulation may be made as needed. Since conditioning effects are relative to the needs of the user, it is a convenience to have adjustable features in formula development to suit the formulator's objectives. Certain users prefer to have as their major objective in hair conditioning excellent detangling of shampooed hair. Others prefer to have less detangling effectiveness but require that their hair feel natural, not overconditioned or heavily coated. Some users like to use clear products; others opaque cremes and lotions. Most users prefer to have their hair free of static charge to allow good manageability. The wide range of physical properties that various betaines and zwitterionic compounds offer are taken advantage of at or about the isoelectric point of hair protein to produce tailor made products that have features that satisfy the user.

As a corollary, it is difficult to measure the attributes of a hair conditioning product with only one parameter describing conditioning. In the evaluation of the present compositions, three parameters may be used to assess hair conditioning effects:

(1) The Rubine Dye Test serves to demonstrate the substantivity of cationic ingredients in hair conditioners. The substantive coating that shows red with Rubine dye is composed of positive charges and/or polarized molecules which tend to conduct ions or electrons (the localized accumulation of such ions or electrons is the cause of static charges). A positive Rubine Dye Test, therefore, indicates that, because of the substantive coating on the hair which is conductive, any accumulating ions or electrons will be mobile and any electrostatic disadvantages to manageability of hair from static electricity are nullified.

(2) Touching hair serves to inform the user the state of conditioning in one's hair. The feeling is totally subjective, varying among individuals according to personal preferences. Some prefer light texture, approaching a natural or unconditioned effect; others prefer the tactile demonstration of conditioning provided by a significant coating of fatty material. In the laboratory evaluation of the "touch" parameter, using a range of 1 to 10, 10 signified a clean feeling, the absence of coating which is apparently present (Rubine Dye Test) and which can offer other advantages; 1 signified a maximum, heavily conditioned coating that can be felt with the fingers. Either effect, a clean feeling or a definitive "conditioned" coating, can be desirable depending on the users perspective.

(3) The ease rendered in combing wet hair after shampooing is perhaps the single most important benefit of creme rinse products. Immediately after shampooing, hair is usually left matted and difficult to comb through. Damage to the hair structure usually results upon combing or brushing at this stage because of the intense friction produced on the tangled hair. Furthermore, pulling and stretching the hair during wet combing result in the weakening of its tensile strength, some degree of hair breakage and in causing pain and discomfort to the individual. The application of a creme rinse balsam or other hair conditioning treatment provides a lubricant coating to the hair shaft that reduces and minimizes the combing effort. The user is thus spared the discomfort of combing tangled and snarled hair. In laboratory evaluation, the effectiveness of a conditioner application in providing easy combing after a shampoo treatment is rated on a 1 to 10 scale. A rating of 10 indicates easy wet combing comparable to the effects of a leading commercial hair conditioner based upon quaternary ammonium surfactants; a rating of 1 indicates the base state of combing hair after shampooing with a detergent cleanser and without a hair conditioner application.

The following procedure may be used to demonstrate the criticality of the pH range of the hair conditioning composition herein and the improvements in wet combing, dry combing and manageability attributable to the pH range herein compared with compositions having higher pH.

2. Procedure for Evaluation (1) 2.5±0.5 g., 10 inch hair swatches are prepared using consistent and uniform hair types (Virgin, Bleached, Grey, etc.).

(2) The hair tresses are collectively shampooed with a 15% active sodium lauryl sulfate solution, using an excess quantity of detergent solution. The hair tresses are carefully handled to avoid excessive tangling during shampooing and are then rinsed free and rendered clean with 40° C. tap water. This process is repeated to simulate a double shampoo application. All test hair tresses are presented in an equivalent clean and "degreased" state.

(3) Individual hair tresses are separated and tagged for test application. Two cc of a test conditioner preparation (excess) is applied to a cleaned, wet tress with a syringe. The conditioner is worked through the hair for one minute with downward strokes of the fingers. The tress is rinsed thoroughly clean under 40° C. tap water for one minute. All test conditioners are treated equivalently. An untreated tress serving as a control is used as a point of reference.

A rating system of 1 to 10 is used in which 1 represents the base state of untreated, difficult-to-manage hair and 10 represents optimum conditioned hair. The rating scale may be used as follows:
10—Highest optimum rating, excellent
9—Good-Excellent
8—Good
7—Fair-Good
6—Average
5—Mediocre
4—Fair-Poor 3—Poor
2—Very Poor
1—Void of Positive Effects A two unit spread is considered readily perceptible and significant.

The evaluation procedure is as follows:

(1) Combing--Hair is combed through, at first, in the wet state then in the dry state, using the fine teeth of a #400 "Cleopatra" comb. Prior to wet combing, excess water is squeezed from the tress in order to simulate tower-dry hair. A rating number is ascribed relative to that of a control tress.

(2) Fly-away--The degree of static charge (on dry hair only) is observed by combing a tress quickly 10 strokes with the coarse teeth of a #400 Cleopatra comb. A rating is assigned relative to a control test.

(3) Manageability is assessed relative to a control by observing its behavior pattern. A rating number is given.

Compositions of the present invention possess excellent conditioning properties as measurable by the foregoing procedures.

I claim:

1. A composition, for conditioning the hair or skin, consisting essentially of
   (a) between about 1.5 and 15 weight percent of an N-alkylcarobxylate-N-fatty alkyl-quaternary amine or -ammonium compound of the formula

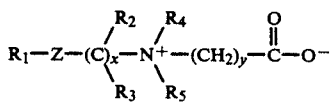

wherein:
   $R_1$ is fatty alkyl;
   x is from 1 to about 3;
   y is from 1 to about 6;
   $R_2$, $R_3$, $R_4$ and $R_5$ are hydrogen, alkyl or hydroxyalkyl;
   $R_4$, $R_5$, $R_6$ and $R_7$ may also form a nitrogen-containing ring together with the carbon and nitrogen atoms to which they are attached; and
   Z represents an amido radical group or a carbon-carbon single bond; and
   (b) between about 0.5 and 5 weight percent of a superfatting material; together with
   (c) acid sufficient to provide a pH between about 2.2 and about 3.2 in said composition.

2. A composition according to claim 1 wherein Z is a single bond, $R_2$ and $R_3$ are hydrogen and $R_4$ and $R_5$ are not hydrogen.

3. A composition of claim 1 wherein Z is an amido radical group.

4. A composition according to claim 1 wherein said superfatting material is selected from the group consisting of fatty acids, fatty alcohols or fatty acid alkyl esters.

5. A composition according to claim 4 wherein aid superfatting material includes cetyl alcohol.

6. A composition according to claim 1 wherein said aminoalkylcarboxylate is one or more of hydrogenated tallow dimethyl glycinate, dihydroxyethyl tallow glycinate or stearamido ethyl ethanolamine glycinate.

7. A method of conditioning hair comprising applying to wet hair an effective conditioning amount of a composition according to claim 1, allowing the composition to become evenly distributed through said hair and rinsing said composition off with water.

* * * * *